US012507752B2

(12) United States Patent
Tseng et al.

(10) Patent No.: US 12,507,752 B2
(45) Date of Patent: Dec. 30, 2025

(54) METHOD OF MAKING GLOVES

(71) Applicant: Inteplast Group Corporation, Livingston, NJ (US)

(72) Inventors: Pai-Mei Tseng, Somerset, NJ (US); Chih Jen Hsu, Closter, NJ (US); Jyh-Yao Raphael Li, Parsippany, NJ (US); Kelvin Yang, Madison, NJ (US)

(73) Assignee: INTEPLAST GROUP CORPORATION, Livingston, NJ (US)

(*) Notice: Subject to any disclaimer, the term of this patent is extended or adjusted under 35 U.S.C. 154(b) by 0 days.

(21) Appl. No.: 18/782,929

(22) Filed: Jul. 24, 2024

(65) Prior Publication Data

US 2024/0373958 A1 Nov. 14, 2024

Related U.S. Application Data

(62) Division of application No. 17/339,650, filed on Jun. 4, 2021, now Pat. No. 12,070,088.

(51) Int. Cl.
*A41D 19/00* (2006.01)
*A61B 42/40* (2016.01)

(52) U.S. Cl.
CPC .......... *A41D 19/0068* (2013.01); *A61B 42/40* (2016.02); *A41D 2400/52* (2013.01)

(58) Field of Classification Search
CPC . A41D 19/0068; A41D 19/0072; A61B 42/40
See application file for complete search history.

(56) References Cited

U.S. PATENT DOCUMENTS

| | | | | |
|---|---|---|---|---|
| 1,538,263 A | | 5/1925 | Ackerman | |
| 3,229,875 A | * | 1/1966 | Stoller | B65D 83/0882 225/53 |
| 3,583,558 A | | 6/1971 | Davis | |
| 3,735,865 A | | 5/1973 | Smith | |
| 3,866,245 A | | 2/1975 | Sutherland | |
| 4,034,853 A | | 7/1977 | Smith | |
| 4,209,857 A | | 7/1980 | Clark, Jr. et al. | |
| 4,677,697 A | * | 7/1987 | Hayes | A41D 19/0068 206/390 |
| 4,804,432 A | | 2/1989 | Jurrius et al. | |
| 4,916,757 A | | 4/1990 | Berlin et al. | |
| 4,928,322 A | | 5/1990 | Bradfield | |
| 5,025,503 A | * | 6/1991 | O'Brien | A41D 19/0068 206/390 |
| 5,244,525 A | | 9/1993 | Neuwirth et al. | |

(Continued)

FOREIGN PATENT DOCUMENTS

| | | | | |
|---|---|---|---|---|
| CN | 201775041 U | * | 3/2011 | |
| GB | 2114871 A | * | 9/1983 | A41D 19/0068 |

(Continued)

*Primary Examiner* — F Griffin Hall
(74) *Attorney, Agent, or Firm* — Stinson LLP

(57) ABSTRACT

A method of making gloves from a web of material, which leaves no scrap from the web of material. A first sheet of material is overlaid on a second sheet of material forming a web. First and second glove patterns are formed in the web are arranged to be opposite one another in the cross machine direction of the web. A sinusoidal cut can be made in the web in the machine direction to form glove patterns opposite each other in the cross machine direction.

11 Claims, 3 Drawing Sheets

(56) References Cited

U.S. PATENT DOCUMENTS

| | | | |
|---|---|---|---|
| 5,246,110 | A | 9/1993 | Greyvenstein |
| 5,611,627 | A | 3/1997 | Belias et al. |
| 6,039,829 | A | 3/2000 | French |
| 6,637,035 | B1 | 10/2003 | Brinkmann et al. |
| 6,748,605 | B1 | 6/2004 | Brinkmann |
| 7,469,427 | B2 | 12/2008 | Yang et al. |
| 7,635,067 | B1 | 12/2009 | Flynn |
| 7,874,455 | B2 | 1/2011 | Jordan et al. |
| 8,132,692 | B2 | 3/2012 | Jordan |
| 8,807,402 | B2 | 8/2014 | Backhaus et al. |
| 9,084,444 | B2 | 7/2015 | Lin et al. |
| 9,084,445 | B2 | 7/2015 | Lin et al. |
| 9,131,737 | B2 | 9/2015 | Lin et al. |
| 9,204,706 | B1 | 12/2015 | Applebee |
| 9,635,892 | B2 | 5/2017 | Lin et al. |
| 2006/0144847 | A1 | 7/2006 | Jordan et al. |
| 2006/0200891 | A1 | 9/2006 | Geraci |
| 2016/0152403 | A1 | 6/2016 | Ray |
| 2020/0323603 | A1 | 10/2020 | Bayly et al. |

FOREIGN PATENT DOCUMENTS

| | | | | |
|---|---|---|---|---|
| KR | 20090067366 | A | * | 6/2009 |
| KR | 101119664 | B1 | * | 3/2012 |

* cited by examiner

METHOD OF MAKING GLOVES

STATEMENT OF RELATED CASES

This application is a divisional of U.S. patent application Ser. No. 17/339,650, filed Jun. 4, 2021, the contents of which is incorporated herein in its entirety.

FIELD

The present disclosure generally relates to a method of making gloves as a matrix of material from which disposable gloves are dispensed.

BACKGROUND

The use of disposable gloves requires in manufacturing, food handling and other contexts requires a substantial number of gloves to be available. Therefore, the manner in which the gloves are contained and dispensed affects their utility. Still further, the cost of gloves must remain low in order to justify the use of large number of gloves.

SUMMARY

In one aspect, a glove matrix containing a multiplicity of disposable gloves generally comprises a first sheet of material and a second sheet of material overlain with the first sheet of material to form a web. The web is elongate and has a machine direction parallel to a length of the elongate web and a cross machine direction perpendicular to the machine direction. In a first plurality of glove patterns in the web, each glove pattern of the first plurality of glove patterns is frangibly connected to the web whereby each glove pattern can be detached from the web to form a glove for one hand. In a second plurality of glove patterns in the web, each glove pattern of the second plurality of glove patterns is frangibly connected to the web whereby each glove pattern can be detached from the web to form a glove for one hand. The second plurality of glove patterns is arranged opposite the first plurality of glove patterns in the cross machine direction of the web.

In another aspect, a glove matrix containing a multiplicity of disposable glove generally comprises a first sheet of material that is overlain on a second sheet of material to form a web. The web is elongate and has a machine direction parallel to the length of the elongate web and a cross machine direction perpendicular to the machine direction. In a first plurality of glove patterns in the web, each glove pattern of the first plurality of glove patterns is frangibly connected to the web whereby each glove pattern can be detached from the web to form a glove for one hand. Each glove pattern of the first plurality of glove patterns includes first cut and seal elements at least partially defining finger receptacles in the glove pattern. In a second plurality of glove patterns in the web, each glove pattern of the second plurality of glove patterns is frangibly connected to the web whereby each glove pattern can be detached from the web to form a glove for one hand. Each glove pattern of the second plurality of glove patterns including first cut and seal elements at least partially defining finger receptacles in the glove pattern. A second cut and seal element disposed between the first plurality of glove patterns and the second plurality of glove patterns extends along a sinusoidal curve.

In yet another aspect, a method of manufacturing disposable plastic gloves generally comprises overlaying a first sheet of material on a second sheet of material to create a web. Glove patterns including a first plurality of glove patterns and a second plurality of glove patterns are formed in the web. Each glove pattern of the first plurality of glove patterns and each glove pattern of the second plurality of glove patterns defines the entirety of one glove when separated from the web. The step of forming the glove patterns includes forming first cut and seal elements at least partially defining finger receptacles, and forming a second cut and seal element between the first plurality and second plurality of glove patterns. The glove patterns occupy all of the material of the web a region of the web where the glove patterns are formed, such that there is no scrap material of the web in the region where the glove patterns are formed.

Other objects and features of the present disclosure will be in part apparent and in part pointed out herein.

BRIEF DESCRIPTION OF THE DRAWINGS

Corresponding reference numbers indicate corresponding parts throughout the drawings.

DETAILED DESCRIPTION

Figure 1:
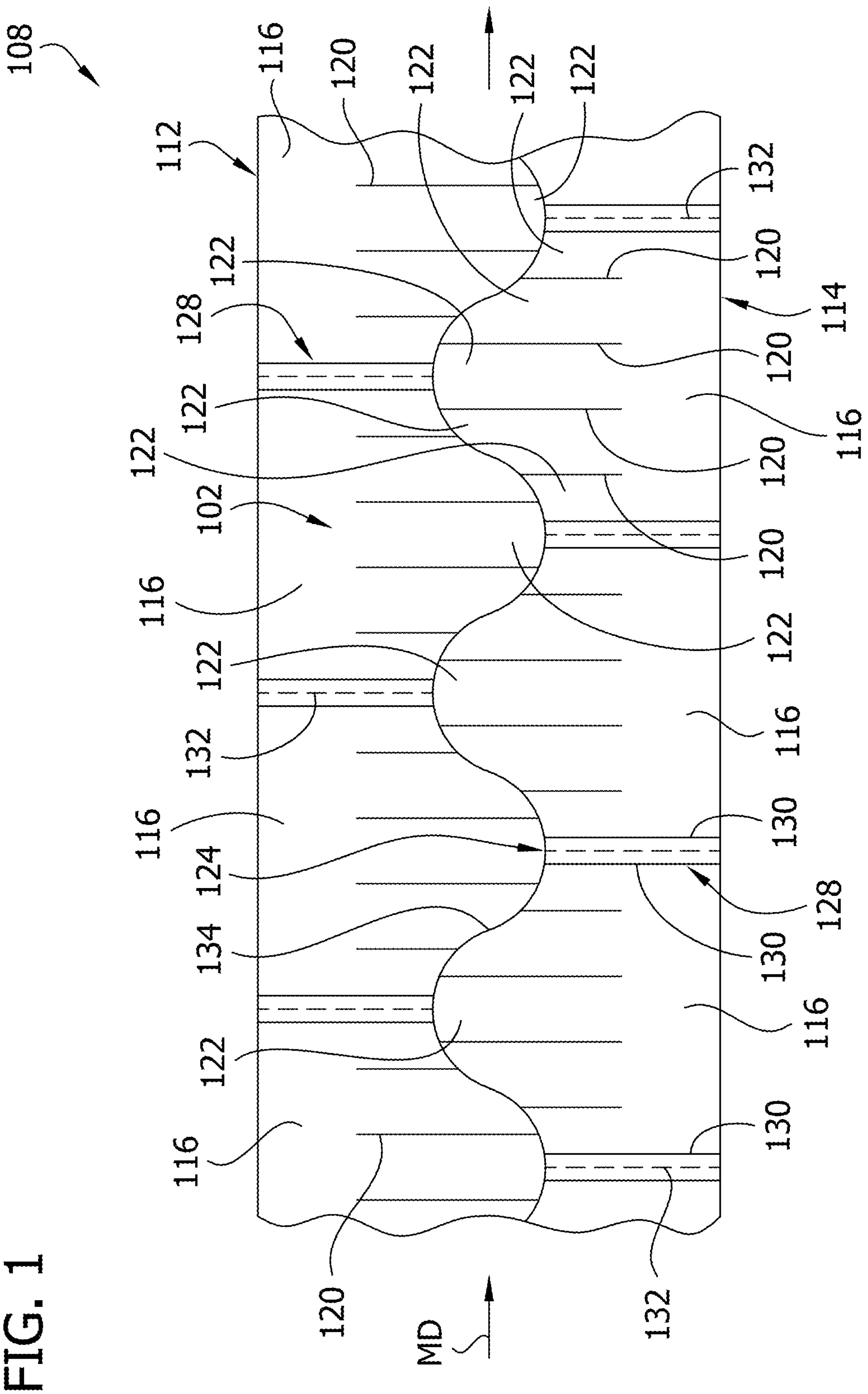
FIG. 1 is a top view of a portion of a fragmentary portion of a glove matrix in the form of a web.
Figure 2:
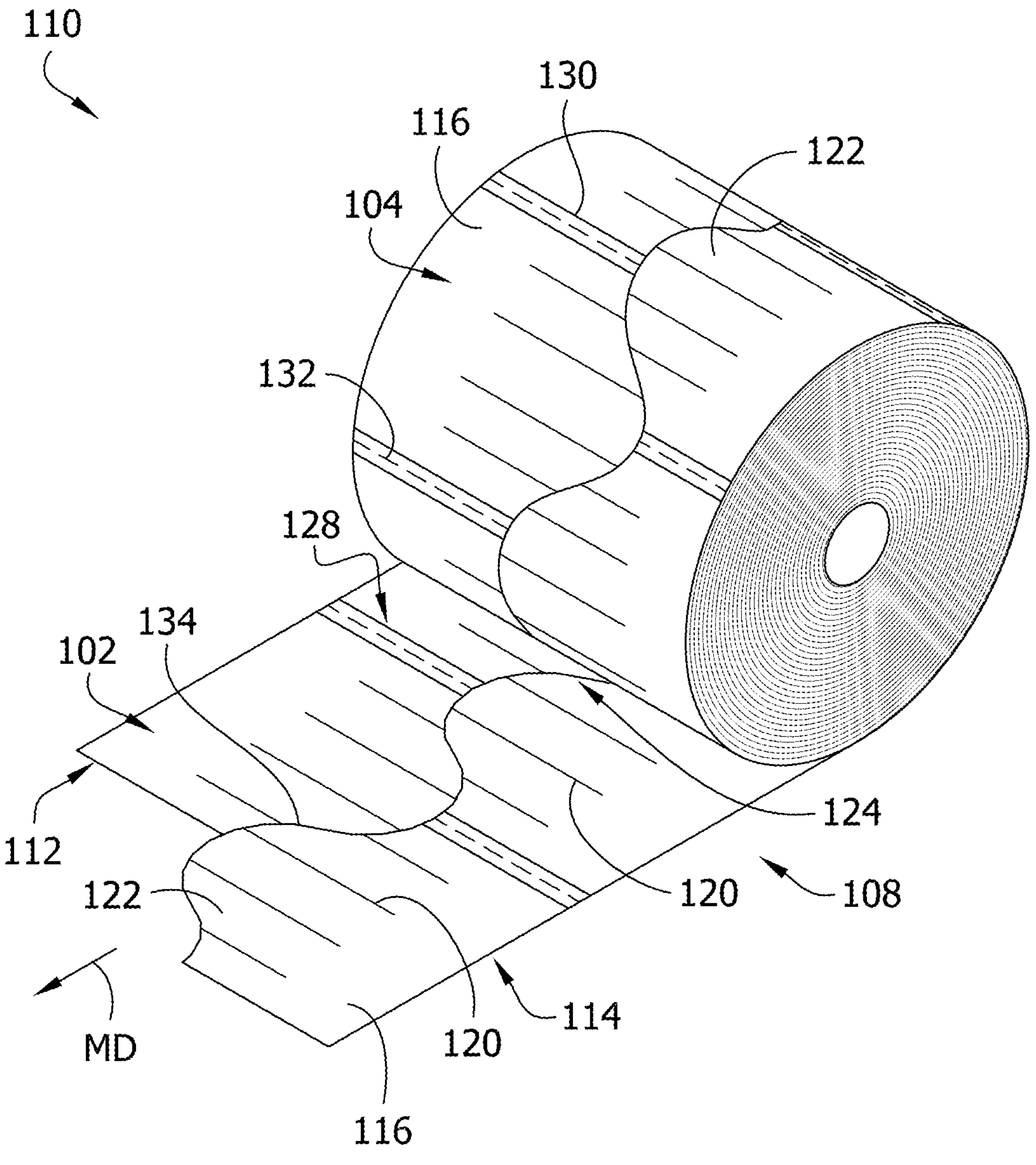
FIG. 2 is a perspective view of the glove matrix in the form of a glove roll.
Figure 3:
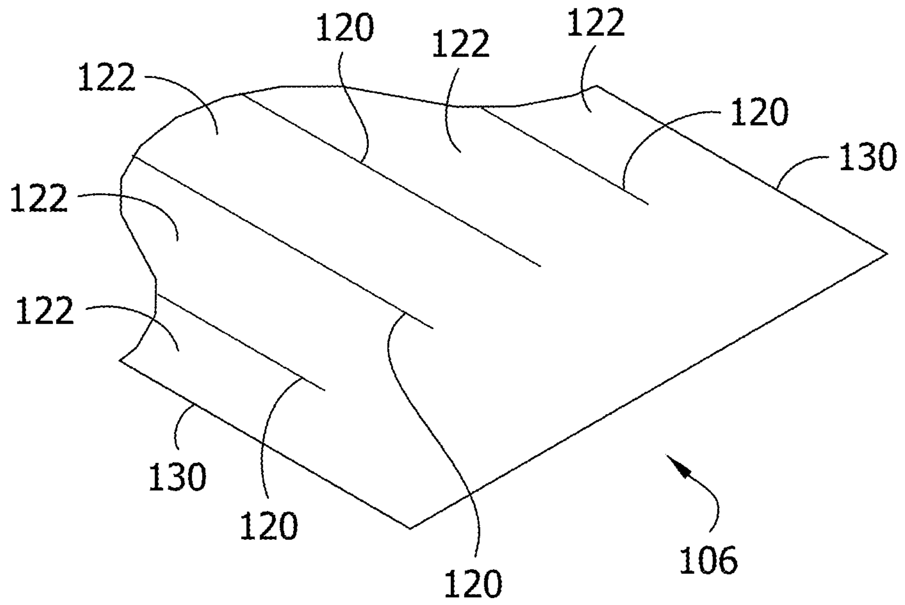
FIG. 3 is a perspective view of a glove separated from the glove roll.

Referring to FIGS. 1-3, a glove matrix is shown to comprise a first sheet 102 of material facing out of the page and a second sheet 104 of material facing into the page (as oriented in FIG. 1). The first and second sheets of material 102, 104 are configured to contain a multiplicity of gloves 106 (FIG. 3). In one embodiment of the disclosure, the first and second sheets of material 102, 104 are made of polyethylene. This disclosure, however, should not be construed to limit the first and second sheets 102, 104 to only polyethylene, as other materials can be used. The second sheet 104 of material is configured to be superposed with the first sheet 102 of material to form a web 108. The first and second sheet 102, 104 can be in registration with each other. Alternatively, the first and second sheet 102, 104 can be configured such that they are not be entirely in registration with each other. For example, when the first and second sheets 102, 104 are not in precise registration with each other, the one of either the first sheet 102 or second sheet 104 is narrower in the cross-machine direction. Thus, a portion of the wider sheet is exposed, which can be utilized by the user to open the web 108. The web is generally elongate and disposed in a glove roll 110. The web 108 has a machine direction MD parallel to the length of the elongate web (generally indicated with an arrow in FIG. 1) and a cross machine direction perpendicular to the machine direction and in the plane of the web. The web 108 has a first plurality of glove patterns 112 and a second plurality of glove patterns 114. Each of the first and second plurality of glove patterns 112, 114 are frangibly connected to the web 108 whereby each glove pattern 116 can be detached from the web to form the glove 106 (FIG. 3) for one hand. The second plurality of glove patterns 114 is arranged opposite the first plurality of glove patterns 112 in the cross machine direction of the web 108. The glove roll 110 will be broadly understood as being the glove matrix in this embodiment. Broadly, a glove matrix contains the first and second pluralities of glove patterns 112, 114, but does not necessarily take the form of a roll. The first and second sheets of material 102, 104 may be made of any suitable material, such as polyethylene. In the illustrated embodiment, the first and second sheets of material 102, 104 are made of the same material, but it will be understood that the first and second sheets of material could be made from different materials. In some embodiments, exterior surfaces of the first and second sheets of material 102, 104 may be treated. For example, the exterior surface of the first sheet of material 102 may be treated so that it does not adhere to another sheet of like material. This allows the web 108 to be unrolled easily without sticking or tearing. On the other hand, the exterior surface of the second sheet of material 104 may be treated so as to enhance the tackiness of the surface, which can aid in grasping and holding onto articles.

Each of the glove patterns 116 of the first plurality of glove patterns 112 and each of the glove patterns of the second plurality of glove patterns 114 comprise first cut and scal elements 120 shaped and arranged to at least partially define discrete receptacles 122 (i.e., finger receptacles) for the fingers of a hand. Each of the first cut and seal elements 120 are formed by a cut through the first and second sheets of material 102, 104 and a seal along the cut joining the first and second sheets of material. It will be understood that although first cut and seal elements are described as being plural, that the term is to be construed to cover forming these elements by a single act of cutting and/or a single act of sealing, or any combination of cutting and scaling acts. The cuts of the illustrated embodiment separate the finger receptacles 122 from the web 108. However, the cuts could be such (e.g., as with perforations or another zone of weakness) that they leave the finger receptacles 122 connected to the web 108 for later separation by tearing along the cut. The first cut and seal elements 120 extend in the cross machine direction. In the illustrated embodiment, some of the first cut and seal elements 120 have different lengths, i.e., one first cut and seal element may be longer than another first cut and seal element. The first cut and seal elements 120 are designed to have varying lengths in order to correspond with the variation in the length of the finger that will be inserted into corresponding discrete receptacle 122. The first cut and seal elements 120 further have first and second ends. The first ends of the first cut and seal elements 120 are most proximate one longitudinal edge of the web 108. The first ends terminate at locations spaced in the cross machine direction from the one longitudinal edge of the web 108. The second ends of the first cut and seal elements 120 are opposite the first ends, and are spaced farther from the one longitudinal edge of the web 108 than the first ends. The second ends lie along a generally sinusoidal curve 124.

Each glove pattern 116 of the first plurality and second plurality of glove patterns 112, 114 further comprises separation regions 128. Each of the separation regions 128 are configured to separate a respective one of the glove patterns 116 from an adjacent one of the glove patterns. The separation regions 128 further comprise a glove side seal 130 and a line of weakness 132 (e.g., perforations). Adjacent glove patterns 116 in the first plurality of glove patterns 112 and a second plurality of glove patterns 114 are configured to share a line of weakness 132. By tearing along the shared line of weakness 132, the adjacent glove patterns 116 are separable from each other. It will be understood that the separation regions 128 may entirely disconnect an individual glove pattern of the first and second glove patterns 112, 114 from the web 108. For example, in some instances it is desirable to form individual gloves 106 which retain no attachment to the web at the time the glove patterns 112, 114 are formed.

Extending in the machine direction MD of the web 108 of the glove roll 110 is a second cut and seal element 134. The second cut and seal element 134 is formed by a cut through the first and second sheets of material 102, 104 and sealed along the cut joining the first and second sheets of material. It will be understood that although the second cut and seal element 134 is describe as being singular, as used herein “second cut and seal element” can be formed by a single cut and/or single seal, by plural cuts and/or plural seals or some combination thereof. The second cut and seal element 134 forms a boundary distinguishing the glove patterns 116 of the first plurality of glove patterns 112 from the glove patterns of the second plurality of glove patterns 114. The second cut and seal element 134 is extends along the sinusoidal curve 124 and defines a distal ends of the finger receptacles 122. The individual glove patterns 116 of the first plurality of glove patterns 112 are offset in the machine direction MD from the individual glove patterns of the second plurality of glove patterns 114. In this way, glove patterns 116 having finger receptacles 122 of lengths approximating the lengths of human fingers and be easily formed with simple, repeatable oscillation of a cutting or slitting knife (not shown) or of the web 108 to form a cut along the sinusoidal curve 124. In the illustrated embodiment, the offset is configured such that the middle discrete receptacle 122 of a glove 106 of the first plurality of glove patterns 112 matches up with the line of weakness 132 of two adjacent gloves of the second plurality of glove patterns 114. None of the first cut and seal elements 120 of the first plurality of glove patterns 112 is aligned with any first cut and seal element of the second plurality of glove patterns 114. However, other configurations are contemplated by this disclosure.

Referring to FIG. 2, as a user pulls on the web 108, the first and second plurality of glove patterns 112, 114 become accessible to the user. In order to detach a glove 106 from the first or second plurality of glove patterns 112, 114, the user must apply force to the glove pattern 116 to the line of weakness 132 shared by adjacent glove pattern. In one embodiment of the disclosure, the second cut and seal element 134 has completely separated the first plurality of glove patterns 112 from the second plurality of glove patterns 114 such that the user must only break the connection at the line of weakness 132 between adjacent glove patterns 116 in order to separate a glove 106. When the first plurality of glove patterns 112 is separated from the second plurality of glove patterns, the first plurality of glove patterns 112 can be rolled into a first glove roll and the second plurality of glove patterns 114 can be rolled into a second glove roll. In another embodiment of the disclosure (not shown), the second cut and seal element 134 has not completely separated the first plurality of glove patterns 112 from the second plurality of glove patterns 114, such that, either before or after the user has broken the connection between adjacent glove patterns 116, the user must also break the connection between the first and second plurality of glove patterns. Referring to FIG. 3, the glove 106 is shown separated from the glove roll 110. The glove 106 is preferably configured to contain five (5) discrete receptacles 122. However, it will be understood that the glove 106 can also have any number of receptacles 122, typically between one (1) and (5). Due to the generally sinusoidal curve of the second cut and seal element 134, the discrete receptacles 122 are shaped in such a way that the side of the receptacle that is closer to the center of the glove 106 is longer than the side of the receptacle that is further from the center of the glove, with the exception of the center receptacle, which is longest at the center of the receptacle. When the glove 106 is separated from the glove roll 110, the user is now able to insert their hand into the glove to protect the hand from contamination or from contaminating other items. In the portion of the glove 106 that lies along the longitudinal edge of the web 108 in the glove roll 110, the first and second sheets of material 102, 104 are not joined together. Thus, the user inserts their hand into the glove 106 by separating the first sheet of material 102 from the second sheet of material 104 on the edge of glove opposite the discrete receptacles 122 to create a cavity into which the hand can be inserted. The discrete receptacles 122 are configured to receive individual fingers of the user when the hand is inserted into the cavity. The seals of the first cut and seal elements 120 form the side boundaries of the three discrete receptacles 122 in the middle of the glove 106 and the inner boundaries of the two discrete receptacle on the edges of the glove, while the outer boundaries of the discrete receptacles on the edges of the glove are formed by the glove side seal 130. The ends of the discrete receptacles 122 are sealed by the seal of the second cut and seal element 134.

An exemplary method of manufacturing gloves 106 (e.g., disposable plastic gloves) will now be briefly described below. The method of manufacturing the glove roll 110 comprises superposing a first sheet of material 102 on a second sheet of material 104 to create a web 108. The method further comprises forming a first plurality of glove patterns 112 and second plurality of glove patterns 114 through a first cut and seal element 120, a second cut and seal element 134, and a separation region 128. The first cut and seal elements 120 at least partially define finger receptacles 122. The second cut and seal element 134 is a generally sinusoidal cut, and separates the first plurality of glove patterns 112 from the second plurality of glove pattern 114. The separation region 128, further configured of a glove side seal 130 and a line of weakness 132 (e.g., perforations), is configured to separate a respective one of a glove pattern 116 from an adjacent one of a glove pattern. After forming the first and second plurality of glove patterns 112, 114, the web 108 is rolled into a glove roll 110 to allow for the dispensing of a gloves 106. Finally, a glove 106 can be formed by tearing a glove pattern 116 from either of the first or second plurality of glove patterns 112, 114.

In another embodiment of the method, the first and second plurality of glove patterns 112, 114 are separated upon manufacture, or at some point prior to shipment. In some instances, the first and second glove patterns 112, 114 are separated from the web 108 upon formation of the glove patterns. It will be understood that the web 108 may be rolled into a glove roll 110 only temporarily, or may never be formed into the glove roll 110 illustrated herein. As previously stated, another option is to roll the glove patterns 112, 114 into separate rolls. In yet another embodiment of the method, instead of rolling the first plurality of glove patterns 102 or second plurality of glove patterns 104 into the glove roll 108, the second cut and seal elements 134 and the line of weakness 132 completely separate the individual glove patterns 116 into gloves 106 as the gloves are formed. The gloves 106 are separated from the web 108 upon formation, or at some time prior to packaging. The separated gloves 106 are stacked in a container (not shown). In any of the preceding embodiments of the method described herein, once every glove 106 has been torn off of web 108, no scrap material will remain. Stated another way, in the region of the web 108 where glove patterns are formed, no material remains of the web after the gloves 106 are formed by separating the first and/or second glove patterns from the web. Of course, the region of the web 108 where first and second glove patterns 112, 114 are formed may include the entirety of the web or something less than the entirety of the web. It will be understood that in some embodiments of the invention, scrap could be left over after formation of the gloves, but the preferred outcome is that no scrap remains from the web 108.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively, or in addition, a component may be implemented by several components.

The above description illustrates the aspects of the invention by way of example and not by way of limitation. This description enables one skilled in the art to make and use the aspects of the invention, and describes several embodiments, adaptations, variations, alternatives and uses of the aspects of the invention, including what is presently believed to be the best mode of carrying out the aspects of the invention. Additionally, it is to be understood that the aspects of the invention are not limited in its application to the details of construction and the arrangement of components set forth in the following description or illustrated in the drawings. The aspects of the invention are capable of other embodiments and of being practiced or carried out in various ways. Also, it will be understood that the phraseology and terminology used herein is for the purpose of description and should not be regarded as limiting.

It will be apparent that modifications and variations are possible without departing from the scope of the invention defined in the appended claims. As various changes could be made in the above constructions and methods without departing from the scope of the invention, it is intended that all matter contained in the above description and shown in the accompanying drawings shall be interpreted as illustrative and not in a limiting sense.

In view of the above, it will be seen that several advantages of the aspects of the invention are achieved and other advantageous results attained.

The Abstract and Summary are provided to help the reader quickly ascertain the nature of the technical disclosure. They are submitted with the understanding that they will not be used to interpret or limit the scope or meaning of the claims. The Summary is provided to introduce a selection of concepts in simplified form that are further described in the Detailed Description. The Summary is not intended to identify key features or essential features of the claimed subject matter, nor is it intended to be used as an aid in determining the claimed subject matter.

What is claimed is:

1. A method of manufacturing disposable plastic gloves, the method comprising:

overlaying a first sheet of material on a second sheet of material to create a web having a lengthwise extent in a machine direction and a widthwise extent in a cross machine direction;

forming glove patterns including a first plurality of glove patterns and a second plurality of glove patterns in the web, each glove pattern of the first plurality of glove patterns and each glove pattern of the second plurality of glove patterns defining the entirety of one glove when separated from the web;

wherein the step of forming the glove patterns includes forming first cut and seal elements at least partially defining finger receptacles, forming a second cut and seal element extending in the machine direction of the web between the first plurality of glove patterns and the second plurality of glove patterns, the second cut and seal element separating the first plurality of glove patterns from the second plurality of glove patterns on opposite sides of the web in the cross machine direction;

whereby the glove patterns occupy all of the material of the web in a region of the web where the glove patterns are formed, such that there is no scrap material of the web in the region where the glove patterns are formed; and wherein the second cut and seal element extends continuously in the machine direction of the web between the first plurality of glove patterns and the second plurality of glove patterns.

2. The method as set forth in claim 1, wherein forming the glove patterns comprises forming the first and second pluralities of glove patterns so that the glove patterns in the first plurality of glove patterns at least partially register with glove patterns of the second plurality of glove patterns in the cross machine direction.

3. The method as set forth in claim 1, wherein forming the second cut and seal element comprises forming a cut in the web having a sinusoidal shape.

4. The method as set forth in claim 1 wherein the step of forming the glove patterns further comprises forming a first glove side line of weakness between each adjacent glove patterns of the first plurality of glove patterns and forming a second glove side line of weakness between each adjacent glove patterns of the second plurality of glove patterns.

5. The method as set forth in claim 4 wherein the step of forming the glove patterns includes forming the first glove side lines of weakness and the second glove side lines of weakness so that the first glove side lines of weakness are offset in a machine direction from the second glove side lines of weakness.

6. The method as set forth in claim 1 wherein the step of forming the glove patterns comprises forming the finger receptacles of the first plurality of glove patterns to be sized and shaped for receiving fingers of a human hand, each of the finger receptacles of the first plurality of glove patterns having a distal end, and forming the finger receptacles of the second plurality of glove patterns to be sized and shaped for receiving fingers of a human hand, each of the finger receptacles of the second plurality of glove patterns having a distal end, and arranging the first plurality of glove patterns and the second plurality of glove patterns in the web so that the distal ends of the finger receptacles of the first plurality of glove patterns are located opposite to the finger receptacles of the second plurality of glove patterns in the cross machine direction of the web.

7. A method of manufacturing disposable plastic gloves, the method comprising:

overlaying a first sheet of material on a second sheet of material to create a web having a lengthwise extent in a machine direction and a widthwise extent in a cross machine direction;

forming glove patterns including a first plurality of glove patterns and a second plurality of glove patterns in the web, each glove pattern of the first plurality of glove patterns and each glove pattern of the second plurality of glove patterns defining the entirety of one glove when separated from the web;

wherein the step of forming the glove patterns includes forming first cut and seal elements at least partially defining finger receptacles, forming a sinusoidal second cut and seal element extending in the machine direction of the web between the first plurality and second plurality of glove patterns; and wherein the second cut and seal element comprises a line extending in the machine direction and having plural oscillations in the cross machine direction as it extends in the machine direction.

8. The method as set forth in claim 7, wherein forming the glove patterns comprises forming the first and second pluralities of glove patterns so that the glove patterns in the first plurality of glove patterns at least partially register with glove patterns of the second plurality of glove patterns in the cross machine direction.

9. The method as set forth in claim 7 wherein the step of forming the glove patterns further comprises forming a first glove side line of weakness between each adjacent glove patterns of the first plurality of glove patterns and forming a second glove side line of weakness between each adjacent glove patterns of the second plurality of glove patterns.

10. The method as set forth in claim 9 wherein the step of forming the glove patterns includes forming the first glove side lines of weakness and the second glove side lines of weakness so that the first glove side lines of weakness are offset in the machine direction from the second glove side lines of weakness.

11. The method as set forth in claim 7 further comprising, following the step of forming the first and second pluralities of glove patterns of forming the web into a roll.

* * * * *